US00PP28436P3

(12) United States Plant Patent
Meilland

(10) Patent No.: US PP28,436 P3
(45) Date of Patent: Sep. 26, 2017

(54) CLIMBING ROSE PLANT NAMED 'BAIPEACESAR'

(50) Latin Name: *Rosa hybrida*
Varietal Denomination: Baipeacesar

(71) Applicant: CP DELAWARE, INC., Wilmington, DE (US)

(72) Inventor: Alain A. Meilland, Antibes (FR)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 14/757,361

(22) Filed: Dec. 22, 2015

(65) Prior Publication Data

US 2017/0034971 P1 Feb. 2, 2017

(30) Foreign Application Priority Data

Jul. 27, 2015 (QZ) ..... PBR 2015/1769

(51) Int. Cl.
*A01H 5/02* (2006.01)

(52) U.S. Cl.
USPC ..... Plt./109

(58) Field of Classification Search
USPC ..... Plt./109
CPC ..... A01H 5/0222
See application file for complete search history.

*Primary Examiner* — Kent L Bell
(74) *Attorney, Agent, or Firm* — Buchanan Ingersoll & Rooney PC

(57) ABSTRACT

A new and distinct Climbing rose plant is provided that forms on a substantially continuous basis attractive blossoms having a blend of yellow and carmine pink coloration. The vegetation is dense dark green and very strong, and bears a glossy aspect on the upper surface. The plant has been found to grow well on its own roots. No particular disease problem has been observed during observations to date. The plant is particularly well suited for providing attractive ornamentation in parks and gardens.

1 Drawing Sheet

Figures 1, 2, 3, 4, 5, 6, 7, 8, 9, 10, 11, 12, 13, 14, 15:
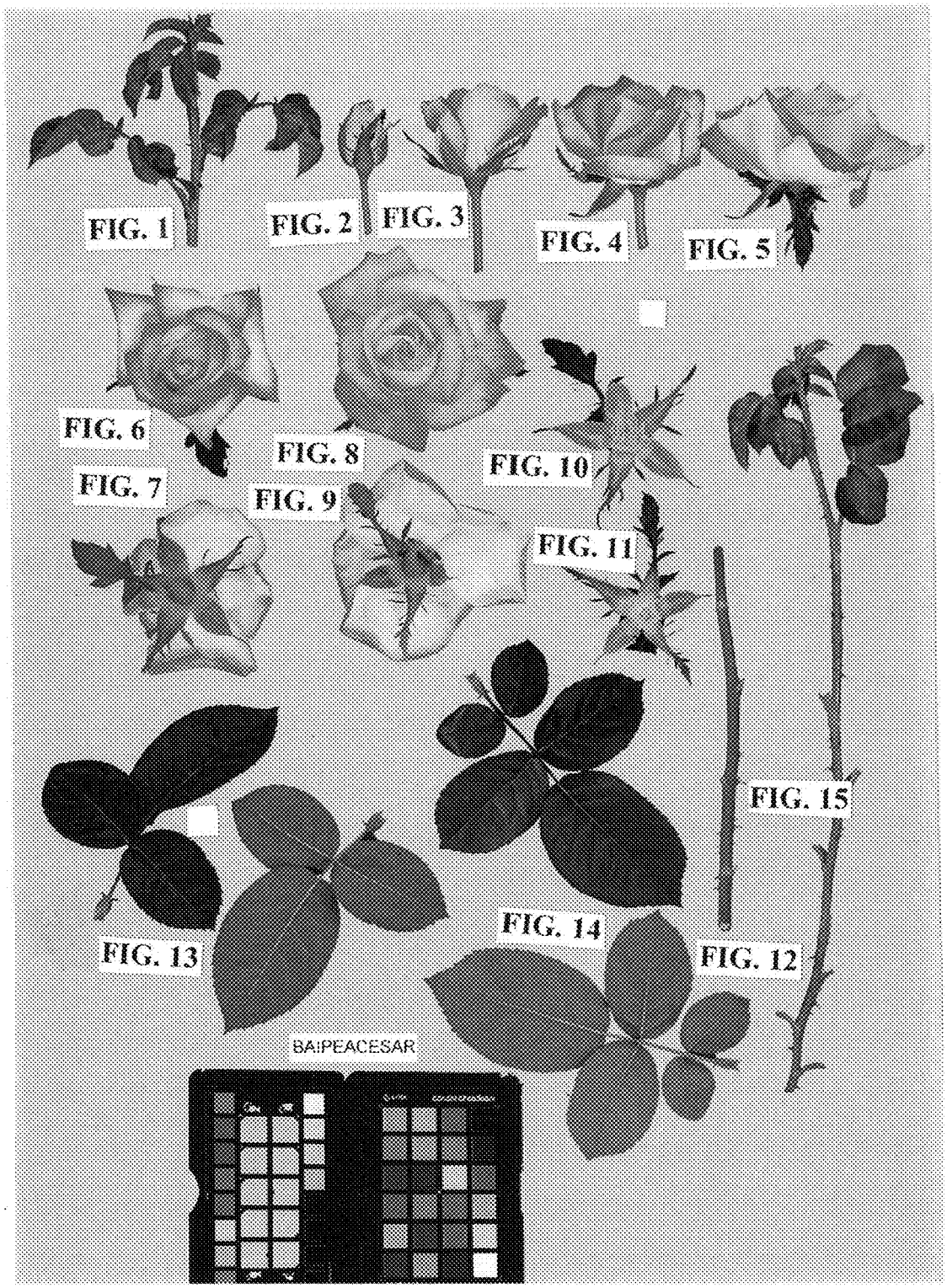

Botanical/commercial classification: *Rosa hybrida*/ Climbing Rose Plant.

Varietal denomination: cv. Baipeacesar.

SUMMARY OF THE INVENTION

The new variety of *Rosa hybrida* Climbing rose plant was discovered in France during 2013 as a spontaneous mutation of unknown causation of the 'Baipeace' variety (U.S. Plant Pat. No. 14,731, granted Apr. 27, 2004). The discovery was made primarily in view of the distinctive climbing growth habit that was displayed in a plant nursery setting tended by man. Had the new plant not been discovered and preserved it would have been lost to mankind.

It was found that the new rose plant of the present invention:

(a) displays a climbing growth habit with very strong vegetation,
(b) forms in abundance on a substantially continuous basis attractive double blossoms exhibiting a blend of yellow and carmine pink coloration,
(c) grows well on its own roots,
(d) exhibits attractive dense dark green foliage with a glossy aspect on the upper surface, and
(e) is particularly well suited for providing attractive distinctive ornamentation in parks and gardens.

The blooming tends to commence early in the season during observations to date. The blossoms coloration contrasts nicely with that of the dark green foliage.

The new variety well meets the needs of the horticultural industry and can be grown to advantage where attractive ornamentation is to be provided.

The new variety can be readily distinguished from its 'Baipeace' parent in view of the dissimilar growth habit. More specifically, the 'Baipeace' variety displays an unlike upright growth habit.

The new variety has been found to undergo asexual propagation in France by a number of routes, including budding, grafting, and the use of cuttings. Asexual propagation by the above-mentioned techniques at Le Cannet des Maures, Var, France, has shown that the characteristics of the new variety are stable and are strictly transmissible by such asexual propagation from one generation to another. Accordingly, the new variety undergoes asexual propagation in a true-to-type manner. The plant grows well on its own roots.

The new variety has been named 'Baipeacesar'.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during June while growing outdoors on their own roots at Le Cannet des Maures, Var, France. Comparative standard color information is included at the base of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a flower in the course of the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates specimens of leaves with three leaflets—plan view—upper surface (left) and—under surface (right);

FIG. 14—illustrates specimens of leaves with five leaflets—plan view—upper surface (top) and—under surface (bottom); and FIG. 15—illustrates a specimen of a climbing branch.

DETAILED BOTANICAL DESCRIPTION

The chart used in the identification of the colors is that of The Royal Horticultural Society (R.H.S. Colour Chart—1995). The description is based on the observation of one-year-old plants during June while growing outdoors on their own roots at Le Cannet des Maures, Var, France.

Class: Climbing.

Plant:

*Growth habit*.—Climbing.

*Size*.—Commonly in excess of 2.2 m of growth is produced in a growing season, with the 'Baipeace' parent commonly assuming an upright height of 1 to 1.5 m under the same growing conditions.

Branches:

*Color*.—Young stems: near Green Group 138B more or less suffused with near Red Group 46A. Adult wood: near Green Group 138B.

*Thorns*.—On young stems: Small prickles: Configuration: with an obovate base. Quantity: approximately 5 on average on a stem length of 10 cm. Length: approximately 3 mm on average. Color near Greyed-Orange Group 164A amply suffused with near Red Group 46A. Long prickles: Configuration: with an obovate to longish base. Quantity: approximately 2 on average on a stem length of 10 cm. Length: approximately 4 mm on average. Color: near Greyed-Orange Group 164A more or less suffused with near Red Group 46A. On adult stems: Small prickles: Configuration: elongated and curved downwards on the upper surface and slightly concave on the under surface with an obovate base. Quantity: approximately 3 on average over a stem length of 10 cm. Length: approximately 3 mm on average. color: near Greyed-Orange Group 164A. Long prickles: Configuration: elongated and curved downwards on the upper surface and slightly concave on the under surface with an obovate and longish base. Length: approximately 4 cm on average. Quantity: approximately 4 on average. Color: near Greyed-Orange Group 164A.

Leaves:

*Stipules*.—Adnate, pectinate, rather broad, approximately 1.2 cm in length on average, approximately 2 mm in width on average, near Yellow-Green Group 144C on the upper surface, and near Yellow-Green Group 144C on the under surface.

*Petioles*.—Upper surface: near Yellow-Green Group 147B in coloration. Under surface: near Yellow-Green Group 144A in coloration. Size: length: approximately 3 to 4 cm on average; diameter: approximately 1-2 mm on average. Texture: non-glandular on the upper surface, and commonly with a few prickles on the under surface.

*Rachis*.—Size: commonly approximately 3.5-5 cm in length and approximately 1 mm in diameter, on average. Coloration: on upper surface the coloration is near Yellow-Green Group 147B sometimes is suffused with near Red Group 46B, and under surface the coloration is near Green Group 143B.

*General appearance*.—Very dense with a glossy aspect on the upper surface of the leaflets.

*Leaflets*.—Number 3, and most often 5 and 7. Shape: with a generally elliptical tip and a rounded base. Size: the terminal leaflets commonly are approximately 7.6 cm in length on average and approximately 4.7 cm in width on average. Apex: generally cuspidate and symmetrical. Base: obtuse. Serration: slightly denticulate, small and single. Texture: physically thick and leathery. Color (young foliage): Upper surface: near Yellow-Green Group 146A and more or less suffused with near Red Group 46A. Under surface: near Yellow-Green Group 146B. Color (adult foliage): Upper surface: near Green Group 139A. Under surface: near Yellow-Green Group 147B.

Inflorescence:

*Number of flowers*.—Commonly one blossom per stem.

*Peduncle*.—Generally smooth, approximately 5 cm in length on average, approximately 3 mm in diameter on average, and near Green Group 138A in coloration.

*Sepals*.—Upper surface: tomentose and near Green Group 138B more or less suffused with near Red Group 46B in coloration. Under surface: tomentose and near Green Group 138A in coloration. Shape: longish and narrow at the tip and commonly upright at the base. Size: approximately 3 cm in length and 1.2 cm in width on average.

*Buds*.—Shape: substantially conical. Size: medium. Length: approximately 2 cm on average. Diameter: approximately 2.4 cm on average. Color as calyx breaks: Upper surface: near Yellow Group 12A and 12B and margined and suffused on the external petals with near Red-Purple Group 58B to 58D. Under surface: near Yellow Group 12B and margined and suffused on the external petals with Red-Purple Group 58C.

*Flower*.—Shape: cup-shaped. Diameter commonly approximately 13 to 14 cm on average when open. Depth: commonly approximately 4.5 cm on average when open. Color (in the course of opening): Upper surface: near Yellow Group 12A and 12B margined and suffused on the external petals with Red-Purple Group 58B and 59D. Under surface: near Yellow Group 12B margined and suffused on the external petals with Red-Purple Group 58C. Color (open flower): Upper side: near Yellow Group 11A margined and suffused on the external petals with near Purple Group 57B. Under side: near Yellow Group 10A and 11A margined and suffused on the external petals with near Red-Purple Group 57C and 57D. Fragrance: slight. Petal number: approximately 49 to 52 on average under normal growing conditions. Petal texture: leathery and somewhat firm. Petal arrangement: imbricated, and without petaloids. Petal tip: commonly reflected. Petal base: obovate. Petal drop: good with the petals commonly detaching cleanly before drying. Stamen number approximately 179 on average. Anthers: regularly arranged around the styles and near Yellow-Orange Group 21A and 21B in coloration. Filaments: near Yellow-Orange Group 14C in coloration. Pollen: present; near Greyed-Yellow Group 160C in coloration. Pistils: approximately 162 on average. Stigmas: approximately 0.8-1 mm in width and approximately 2 mm in length on average, and near Yellow-Green Group 150D in coloration. Styles: near Yellow-Green Group 150D in coloration. Receptacle: smooth, funnel-shaped in longitudinal section, and near Green Group 138A in coloration.

Development:

*Vegetation*.—Very strong.

*Blooming*.—Early season, very abundant and substantially continuous from May through first frost.

*Tolerance to diseases*.—Good, with no particular susceptibility to common diseases having been encountered during observations to date. The new 'Baipeacesar' variety has not been observed under all possible environmental conditions to date. Accordingly, it is possible that the phenotypic expression may vary somewhat with changes in light intensity and duration, cultural practices, and other environmental conditions.

I claim:

1. A new and distinct rose plant characterized by the following characteristics:

(a) displays a climbing growth habit with very strong vegetation, (b) forms in abundance on a substantially continuous basis attractive double blossoms exhibiting a blend of yellow and carmine pink coloration, (c) grows well on its own roots, (d) exhibits attractive very dense dark green foliage with a glossy aspect on the upper surface, and (e) is particularly well suited for providing attractive distinctive ornamentation in parks and gardens;

substantially as shown and described.

* * * * *

BAIPEACESAR